United States Patent [19]

Linner

[11] Patent Number: 4,510,169

[45] Date of Patent: Apr. 9, 1985

[54] METHOD AND APPARATUS FOR CRYOPREPARING BIOLOGICAL TISSUE FOR ULTRASTRUCTURAL ANALYSIS

[75] Inventor: John G. Linner, Houston, Tex.

[73] Assignee: The Board of Regents, The University of Texas, Austin, Tex.

[21] Appl. No.: 525,626

[22] Filed: Aug. 23, 1983

[51] Int. Cl.³ .................... F26B 5/06; F26B 5/10; A01G 5/06; A01N 1/00

[52] U.S. Cl. ................................. 427/4; 34/5; 62/62; 62/100; 118/50; 378/208; 424/3; 427/54.1

[58] Field of Search ............ 424/3; 427/4, 54.1; 34/5, 92, 15; 62/64, 78, 62, 268, 514 R, 100; 118/50; 378/208

[56] References Cited

U.S. PATENT DOCUMENTS

| | | | |
|---|---|---|---|
| 3,679,450 | 7/1972 | Beightol | 424/3 X |
| 4,055,904 | 11/1977 | Horne | 34/45 |
| 4,100,158 | 7/1978 | Hydes et al. | 424/3X |
| 4,120,991 | 10/1978 | Ornstein | 424/3X |
| 4,232,453 | 11/1980 | Edelmann | 34/5 X |
| 4,248,821 | 2/1981 | Van Dellen | 264/135 |
| 4,266,111 | 5/1981 | Trillwood | 219/121 EN |
| 4,269,713 | 5/1981 | Yamashita et al. | 210/500.2 |
| 4,278,623 | 7/1981 | Niegisch | 264/28 |
| 4,278,701 | 7/1981 | Hagens | 427/4 |
| 4,331,591 | 5/1982 | Baylis | 260/112.5 R |
| 4,336,691 | 6/1982 | Burstein et al. | 62/64 |
| 4,337,240 | 6/1982 | Sakland | 424/1 |
| 4,379,003 | 4/1983 | Robbins et al. | 148/104 |

OTHER PUBLICATIONS

Sleytr, U. B. and Robards, A. W., "Understanding the Artefact Problem in Freeze-Fracture Replication: A Review", *Journal of Microscopy*, 126, 101–122 (1982).

Terracio, L. and Schwabe, K. G., "Freezing and Drying of Biological Tissue for Electron Microscopy", *Journal of Histochemistry and Cytochemistry*, 29, 1021–1028 (1981).

Primary Examiner—Michael R. Lusignan
Attorney, Agent, or Firm—Arnold, White & Durkee

[57] ABSTRACT

This invention relates to a method for the cryopreparation of biological tissue samples for ultrastructural analysis. The process comprises vitrifying a biological tissue sample under severely rapid conditions and then depressurized. The depressurized, vitrified tissue sample is brought to equilibrium at a temperature of less than −140° C. The tissue sample is then dehydrated while maintained in a state of thermal equilibrium. After reaching equilibrium the tissue sample is infiltrated with a degassed resin and followed by a polymerization of the resin to form an embedded tissue sample. This invention additionally relates to a sample holder apparatus which has unique use characteristics in the process of this invention.

31 Claims, 10 Drawing Figures

METHOD AND APPARATUS FOR CRYOPREPARING BIOLOGICAL TISSUE FOR ULTRASTRUCTURAL ANALYSIS

BACKGROUND OF THE INVENTION

1. Field of the Invention

This invention relates to a method and apparatus for preparing biological tissue samples for ultrastructural analysis by avoiding significant modification of the ultrastructure of tissue during preparation of the samples themselves. It is well known in the medical arts that to examine tissue samples, and determine the cellular structure and function thereof, the tissue must be "fixed" prior to the application of nearly all analytical methodologies.

Although the examination of tissue samples by use of various microscopes or related magnifying apparatus has been practiced for many years, there has been an inherent problem in preparing tissue samples for use with contemporary high resolution analytical microscopes, such as the STEM electron microscopes, which permit the examination of sample constituents via X-ray analysis at powers of from 500× to 500,000× with point to point resolution of 2 to 3 Angstrom units.

Specifically, it is difficult to interpret the results of tissue analysis while concomitantly assessing the extent of various artifacts produced during the tissue preparation processes. It is thus essential that artifacts be avoided wherever possible. Another problem results from physical shrinkage of the tissue sample itself when subjected to the extreme but necessary for successful preparation procedures extent in current dogma. In most normal tissue preparation steps, tissue shrinkage is in the order of 40%-50%. This shrinkage inevitably results in alteration of ultrastructure and massive rearrangement of infrastructural resolution. The net result of this ultrastructural translation damage is inaccurate detail in descriptions via this analytical procedure.

During the so-called "Golden Age of Morphology" the predominant underlying goal in qualitative and quantitative microscopy has been an aesthetically pleasing image. This goal is readily attainable with the fixation methods and apparatus which are currently available. However, it has become essential that the aesthetically pleasing image, which is produced by the preparation process, also yields a tissue sample which accurately reflects the true condition of tissue in the living organism i.e., approaching the "living state". This is the problem which the process and apparatus of this invention address and solve. Magnification apparatus which is currently available for analytical use is technically more advanced than are current tissue preparation technicques which have been previously employed. The method of this invention results in the preparation of tissue samples which are readily usable on known magnification and analytical apparatus.

2. The Prior Art

The most common prior art method for preparation of tissue samples for analysis is by means of chemical fixation and organic solvent dehydration. Inherent in this process is the concomitant artifact creation, sample shrinkage and resultant damage to and modification of tissue characteristics. These modifications, whether in the form of artifacts or the like, require interpretation by the individual or apparatus analyzing or evaluating the sample. This introduces, in many instances, an unsatisfactory risk of error. Chemical fixation is a well known technique and has served the analytical biologist well for many years and undoubtedly will continue to do so in certain limited applications. However, as the use of tissue sample analysis becomes more complex and the use of such analysis becomes more widespread, alternatives to chemical fixation are demanded. This is especially true as advances are being made in the magnification and analytical apparatus which is available. It is necessary that tissue preparation methods and the apparatus necessary to prepare tissue samples be equally advanced as the analytical tools, i.e., electron microscopes, which are being used to analyze the samples. Obviously, if the technology for tissue sample preparation is behind the technology of microscopy then the advanced microscopes serve no purpose to the morphologist or other tissue examiner.

The most common alternative to chemical fixation and organic solvent dehydration is freeze drying cryofixed samples. Freeze-drying following cryofixation is a well documented and well known technique for tissue preservation. It has several advantages. Cryofixation freezedrying results in a near-instantaneous arrest of cellular metabolism. There is also a stabilization and retention of soluble cell constituents through elimination of solvent contact with the sample. These are significant advantages to cryofixation-freeze-drying that have resulted in a great deal of research endeavors in attempting to apply cryofixation and freeze-drying techniques to known tissue preparation processes.

Unfortunately, the use of freeze-drying has resulted in the identification of a number of disadvantages. The primary disadvantage in currently available freeze-drying techniques is prevention of the formation of ice crystals. As can be readily appreciated, the formation of ice crystals destroys the ultrastructural morphological characteristics of the tissue sample being reviewed. The image is distorted when the cytoplasm becomes reticulated. The formation of ice crystals in the sample can also result in a change in pH of the tissue (eutectic formation) which possibly can result in abnormal cross-linking of macromolecules. There is also the possibility that proteins will denature and precipitate. These are but a few of the disadvantages which are inherent in the freeze drying process.

This general topic is discussed in some detail together with other prior art methods in an article entitled "Freezing and Drying of Biological Tissues for Electron Microscopy", Louis Terracio and Karl G. Schwabe, published in *The Journal of Histochemistry and Cytochemistry*, Volume 29, No. 9 at pp. 1021–1028 (1981). Problems associated with artifact formation are described in "Understanding the Artifact Problem in Freeze-Fracture Replication: A Review", *The Royal Microscopial Society*, (1982) at 103–123.

General principles which have been found applicable to freezing techniques which have demonstrated utility in the preparation of tissue samples are that as the cooling rate increases, tissue fluids can be frozen without the separation of water to extracellular spaces. It has been found, however, that regardless of the rate of cooling, ice crystals are probably still formed but as the cooling rates increase the size of the intracellular ice crystals decreases. The small size of ice crystals at high freeze rates is of course a substantial advantage in morphological examination as this results in minimal artifact creation and minimal ultrastructural damage during dehydration.

Historically, the criterion by which the techniques for rapid freezing have been judged was not the cooling rate of the system but simply the temperature of the environment in which the tissue was frozen. Thus, the term rapid freezing has been applied to any system in which the cooling agent has a temperature of −150 degrees C. or below. The effectiveness of a cooling system is dependent upon the rate at which heat is removed from the sample. Heat transfer is dependent not only on the temperature of the freezing system but also on its physical and thermal characteristics, as well as the size and thermal characteristics of the sample.

The most commonly used technique for rapid freezing is to immerse or "quench" the sample in a fluid cooling bath. The most commonly used fluids for quenching are liquid nitrogen, isopentane, propane and fluorocarbons such as Freon 12 and Freon 22. Although liquid nitrogen is generally regarded as an ideal quenching fluid due to its low temperature (−196 degrees C.), there are inherent disadvantages in the use of liquid nitrogen due to the occurrence of tissue surface film boiling due to the low heat of vaporization of liquid nitrogen. Film boiling is a characteristic of liquid nitrogen that inhibits the heat transfer rates by actually insulating the sample.

An alternate prior method for rapid freezing is freezing on the surface of a chilled metal. This typically involves opposing the tissue sample to a polished flat metal surface by pressing it firmly against this surface of the metal. Silver and copper are typically used as the polished metal blocks. This method is designed to take advantage of the high thermal conductivities and heat capacities of these metals when cooled to liquid nitrogen or liquid helium temperatures. The critical step in chilling on the surface of a metal is making firm contact with the dry, chilled metal surface with no rotational, translational or rebounding motion. Certain commercially available apparatus having known utility in the medical arts address and provide "bouncefree" freezing. Credit for the development of this apparatus is generally accorded to Dr. Alan Boyne of the University of Maryland School of Medicine.

There has recently been verification that there is a direct correlation between cooling rate and ultrastructural preservation in quenching fluids. As the freezing rate increases over the range of 100–4100 degrees C. per second (liquid nitrogen - propane), there is a corresponding decrease in the size of ice crystals present and thus an improvement in morphological preservation.

The critical step in the subsequent tissue preparation process is invariably the sublimation - dehydration of the supercooled tissue fluids recently described as an adiabatic "molecular distillation" process. Once the appropriate supercooling method has been chosen and implemented, it is necessary to further process the tissue for microscopic evaluation, since electron microscopes or other magnification apparatus that allow the viewing of frozen hydrated specimens are not readily available. Thus, dehydration is an essential step in the preparation of biological tissue samples and a step which oftentimes results in the destruction via reticulation of the infrastructure and ultrastructure of the tissue morphology.

In certain prior drying techniques, the tissue sample had not been entirely solidified due to eutectic formation as the cellular fluid solutes are concentrated in bound water compartments. This transfer of solute occurs while the materials are in the fluid state when slow cooling is employed. When rapid freezing techniques are used special considerations forthcoming are in the dehydration step. These problems result from the fact that the dehydration must take place (the water must be removed) in the solid rather than the liquid state, i.e. sublimation.

In the prior art, the freeze substitution approach has involved the removal of tissue water by substituting a solvent or solvent-fixative mixture for the water at −75 to −80 degrees C. This introduces less severe solvent phase separation and chemical alteration artifacts to a tissue sample than past chemical fixation methodologies. From a practical standpoint freeze drying is complicated by the requirement that the tissue sample be warmed so as to increase the vapor pressure of the supercooled water and allow sublimation to proceed in a reasonable period of time. The increased temperature, in addition to increasing vapor pressure can produce a series of physical events leading to the expansion of ice crystals and concomitant damage to the ultrastructural morphology of the tissue sample. Many of the physical events which occur during the warming process have to do with transitions in the physical state of the water which is present. Changes which are typically encountered are glass transition, devitrification and recrystallization with an ensuing series of crystal lattice configuration transitions.

Thus it can be appreciated that freeze drying and other cryopreparation techniques present an exceptional opportunity for the preparation of tissue samples for morphological examination. However, inherent in the use of cryopreparation techniques are problems associated with dehydration and fixation of samples. These are the problems which are addressed by the process and apparatus of this invention.

The cryopreparation process of this invention has also demonstrated an extraordinary application in the transplanting of corneal tissue. Prior to this invention attempts to transplant corneas which involved a necessary freezing or freeze-drying of the corneas after removal from the donor invariably resulted in a clouded cornea upon transplanting. This physical condition of the transplanted cornea was caused by crystal formation in the cornea itself and concomitant damage to the stroma. Use of the process of this invention has enabled ophthalmologists to cryoprepare corneas immediately after removal from donors and to then transplant those corneas to the recipients with almost no clouding or crystal formation whatsoever. The ability to so transplant corneas represents an exceptional advantage to the process of this invention as well as a medical breakthrough in corneal transplant surgery.

It is therefore an object of this invention to provide a method for the preparation of biological samples without overt disruption or destruction of the morphological characteristics of the ultrastructure of the tissue sample.

It is a further object of this invention to provide a method for the preparation of tissue samples obtained in the solid vitreous phase by rapid freezing, the freezing process not resulting in unnecessary artifacts which restrict the interpretation by conventional analytical apparatus.

It is a still further object of this invention to provide a method for the preparation of tissue samples which permits the effective dehydration of the samples without corresponding damage to the tissue ultrastructure and which results in samples which can be used with modern high-powered magnification apparatus.

It is an additional object of this invention to provide a sample holder for use in the process of this invention.

These and other objects of this invention will be recognized from the description of the preferred embodiments which follows.

SUMMARY OF THE INVENTION

This invention relates to a method for the cryopreparation of biological tissue samples for ultrastructural analysis. The process comprises adiabatic dehydration of a biological tissue sample under severely depressurized conditions. The depressurized, vitrified tissue sample is brought to equilibrium at a temperature of less than $-140°$ C. The tissue sample is then dehydrated while maintained in a state of equilibrium. After removal of tissue water, the tissue sample is infiltrated with a degassed resin and followed by a polymerization of the resin to form an embedded tissue sample. This invention additionally relates to a sample holder apparatus which has unique use characteristics in the process of this invention.

DESCRIPTION OF THE PREFERRED EMBODIMENTS

In the method for applying this invention it is first a fundamental prerequisite that the desired biological sample is obtained. Biological samples are collected by a variety of means, i.e. surgical extraction, withdrawn blood samples, binders and any of a variety of other techniques which are well known and conventional. The particular method of obtaining the biological sample is not limiting on the process and apparatus of this invention. However, the preparation of the tissue sample in the method and apparatus of this invention is enhanced if the tissue sample is processed as soon after excising as is possible.

It is not possible that the tissue sample can be retained in a fixative, i.e., formaldehyde, or another biologically active stabilizing solution, in an attempt to maintain the sample during shipping, storage or other necessary operations. It is also critical that the sample not be routinely frozen or otherwise physically modified prior to preparation according to the method of this invention. The size of the tissue sample is especially important for this invention. The preparation of the tissue sample takes place immediately as it is received. The sample may later be physically sectioned or otherwise physically prepared for long-term storage in apparatus or use with various currently available commercial analytical apparati.

The preferred optimum biological sample for preparation by the method of this invention is a fresh one cubic millimeter biopsy sample. These samples must be vitrified as soon as possible. By vitrifying or vitrification it is intended to make reference to a process which results in cryofixation of the sample which is different from "frozen". In the process of vitrifying, the freezing apparatus which is used, renders the sample in the vitreous phase such that soluble and insoluble moities contained in the tissue sample are not disturbed, translated, or altered nor are they concentrated (as eutectics). By definition a vitrified liquid will shatter when undergoing a shear stress, e.g. window glass. The vitreous phase involves the conversion of liquid water into an amorphous or "glass" phase. This is accomplished by rapidly supercooling the tissue sample by opposing it "bounce-free" onto the highly polished (mirror-like) surface, condensate free surface of a metal rod maintained at $-196°$ C. These operations have been discussed previously in the prior art section of this disclosure.

Of particular utility in the process and apparatus of this invention is a "bounce-free" freezing apparatus which has been identified in association with Dr. Alan Boyne of the University of Maryland School of Medicine. In this freezing apparatus, a copper block is used to vitrify the tissue sample. This vitrification in conjunction with a supercooled fluid such as liquid nitrogen, helium, propane or the various freons will cause the tissue sample fluids to supercool to the amorphous state before and/or without the formation of noticeable or resolvable cell water ice crystals. It is absolutely essential that the now vitrified tissue sample be maintained at a temperature of less than about $-140$ degrees C. during storage and transfer operations prior to removal of the tissue water.

Depending on the anticipated time lag between freezing of the sample and dehydration of the sample, it may be stored submerged in a liquid nitrogen dewar. Once the sample has been dried and embedded properly it may be stored virtually indefinitely without cytoplasmic reticulation or other forms of cellular catabolism which will cause modifications and translation resulting in undesirable artifacts which render the tissue uninterpretable as analytical data.

After vitrifying, and while maintaining the tissue sample at a temperature of less than $-140$ degrees C. it is transferred via a specimen transport and fed through to a specimen holder in vacuo. The specimen holder (also commonly referred to as a sample holder), is maintained in a temperature controlled container. The container and specimen holder are both maintained at temperatures below $-140$ degrees C. In the most preferred embodiment of this invention, liquid nitrogen temperatures of $-196$ degrees C. are preferably maintained. The reason that $-140$ degrees C. is critical is that pure water, existing in the vitreous phase when at liquid nitrogen temperatures, will begin to initiate cubic ice crystallization at $-140$ degrees C. As has been established in the prior art section of this disclosure, ice crystallization causes ultrastructural damage, i.e. reticulation, to the morphology of tissue samples.

Next, the atmosphere surrounding the tissue sample, specimen holder and container is depressurized. This is typically done by drawing a vacuum on the sample holder. The vacuum is drawn to a level of $3 \times 10^{-9}$ Torr in approximately 300 minutes. In other embodiments of this invention, the vacuum which is drawn is from $3\times10^{-9}$ Torr to $1\times10^{-10}$ Torr accomplished in less than 300 minutes. These pressures remain at $3\times10^{-9}$ Torr throughout the remainder of the prescribed routine until all the tissue water has been removed. Throughout equilibration of the system (24–48 hours), the specimen temperature is maintained by liquid nitrogen while the vacuum is being drawn and maintained.

At this time the tissue sample is at ultra low pressure and exceptionally low equilibrium cryo-temperature. After equilibration is obtained (with equilibrium temperature below $-140°$ C.) the vitreous water which is found in the tissue sample will begin to sublime as energy equal to the heat of sublimation is intermittantly and incrementally supplied to the sublimation front in the tissue. This is a slow process but one which is critical to the preparation of the sample. It is an important requirement that the sample be permitted enough time to allow it to reach equilibrium after each addition of energy. By equilibrate it is meant that the temperature of the tissue sample no longer changes over a 2–4 hour time interval. In a typical tissue preparation process the sample is rapidly vitrified to $-196$ degrees C. and maintained below $-140°$ C. during storage/transfer to the sample holder in the sublimation (drying) apparatus, after appropriate equilibration time the equilibrium temperature will be somewhere between $-140$ degrees C. and $-196$ degrees C. During this entire equilibration process a critical ultra-low pressure is maintained at $3\times10^{-9}$ Torr or below.

After the equilibration process, which is an essential phase in the method of this invention, it would take an exceptional length of time for any appreciable amount of water to evaporate from the sample if no energy (heat) of sublimation were added to the system. Estimates are in terms of years for the water to evaporate at temperatures and pressures which are associated with the method of this invention. Therefore, in the most preferred embodiment of this invention, a secondary energy source (heating) is added to excite the sublimating water molecules without causing damage to the ultrastructure of the dry tissue sample. Radiant energy, having a particular wavelength, is thought to be an especially useful approach to accomplish this goal. Sublimation energy via microwave, laser systems and magnetic energy are also appropriate. The most preferred secondary source is the nuclear magnetic resonance approach in combination with the above. At equilibrium, the temperature of the tissue will not change unless the ambient parameters of the immediate environment (radiant energy predominates i.e., room temperature is 27° C.) change. This is the general identification of the point of system equilibrium.

Subsequent to the tissue sample reaching equilibrium, it is necessary to remove the supercooled solid water and/or presently unresolvable ice crystals (20 nanometers diameter or less) which have formed in the tissue during the vitrification operation. This portion of the dehydration is absolutely critical and is the step where most potential disruption and reticutation of the ultra-structure in the tissue will express itself. This is accomplished by gradually replacing the energy of sublimation in the sample by minimal increments of adiabatic heat (heat) per hour. The optimal condition is to have no tissue temperature increases. By so raising the thermal energy equivalent to the latent heat of sublimation all of the solid water, whether micro-ice crystals or amorphous super cooled water is effectively removed from the tissue sample by the surrounding cryosystem. This drying may be accomplished with temperatures between $-140°$ C. and $-80°$ C. This regimen of greater temperature latitude will provide variable results and is possible at all due to elevation of devitrification temperatures by the solutes that are dissolved in cell water at varying concentrations. With appropriate instrumentation it is possible to determine when all cell water has been removed. At that point, the energy increase can be accelerated to produce a final specimen temperature 3° C. above room temperature (28°–30° C.). Thus, with this instrumentation a significant advantage in the process of this invention is obtained.

The now dehydrated tissue sample has been permitted to reach room temperature plus 3° C. Even though reaching room temperature the vacuum is maintained at the original exceptionally ultra-low levels as has the temperature surrounding the sample. Room temperature for purposes of this application should be understood to be approximately 24–27 degrees C. There may logically be variations in this temperature level.

At this juncture, the investigator has the option of exposing the tissue to osmium vapors for approximately one hour to provide contrast enhancement via electron density. This may be ommitted if proven to be deleterious to the moiety of interest or if the ultimate goal is clinical use. The osmium vapor is removed by recrystallization by cryoprecipitation. In other established fixation processes paraformaldehyde and/or gluteraldehyde in buffer solution is used. These materials are typically referred to as chemical-fixative materials. The most preferred material which is typically added is osmium tetraoxide. This material will enhance the resolution and contrast of the various constituents of the tissue for the various analytical apparatus which might be used to interpret the tissue sample.

A degassed resin is then added to the tissue while still maintaining the depressurized condition. This is typically referred to as resin infiltration and results in an embedded tissue sample. Resins which have shown utility in past methods are equally applicable to the method of this invention.

Subsequent to these steps the tissue sample and resin are brought to atmospheric pressure by slowly admitting air through the resin port. The embedded tissue sample which has resulted from the resin application process is removed and the resin is polymerized at its prescribed temperature. The particular method of polymerization is largely dependent on the resin that is used. Typically, the tissue sample is polymerized by heat application in an oven for twelve hours. A normal temperature would be 60 degrees C. but may be as low as $-80°$ C. if necessary. It is essential that the polymerization step be accomplished without damage to the tissue ultra-structure.

Following polymerization the tissue sample can then be stored at room termpature, thin sectioned stained or further prepared for other analysis. However, having been dehydrated in the fashion disclosed by this invention it is maintained in a cryofixed state which is readily interpretable by conventional ultramicrotomes and electron microscopes and provides the basis for exceptionally meaningful analysis of tissue samples with a significant alteration of and reduction of artifacts concomitantly reducing or eliminating past constraints throughout to be ubiquitous in fixation and/or tissue preparation for visual analysis.

The actual relating of structure to function in these biological tissues is done by routine ultrathin sectioning with an enormous expansion of applicable staining methods heretofore deemed unapproachable via conventional electron microscopy, (i.e. Immunological analysis of any soluable moieties, sugars, lipids and soluble proteins), enzyme cytochemistry within organless, X-ray dispensive STEM analysis, tissue transplant preparations, microprobe analysis, autocobiography (esp. of soluble compounds) and pharmaceutical preparations.

Other apparatus is available for the execution of this hierarchy but none have produced the result expected as they do not incorporate in totality the required, defined parameters discussed earlier. The apparatus which is used in the practice of the method of this invention is illustrated schematically in FIGS. 2 and 3.

Figures 3, 9, 10:
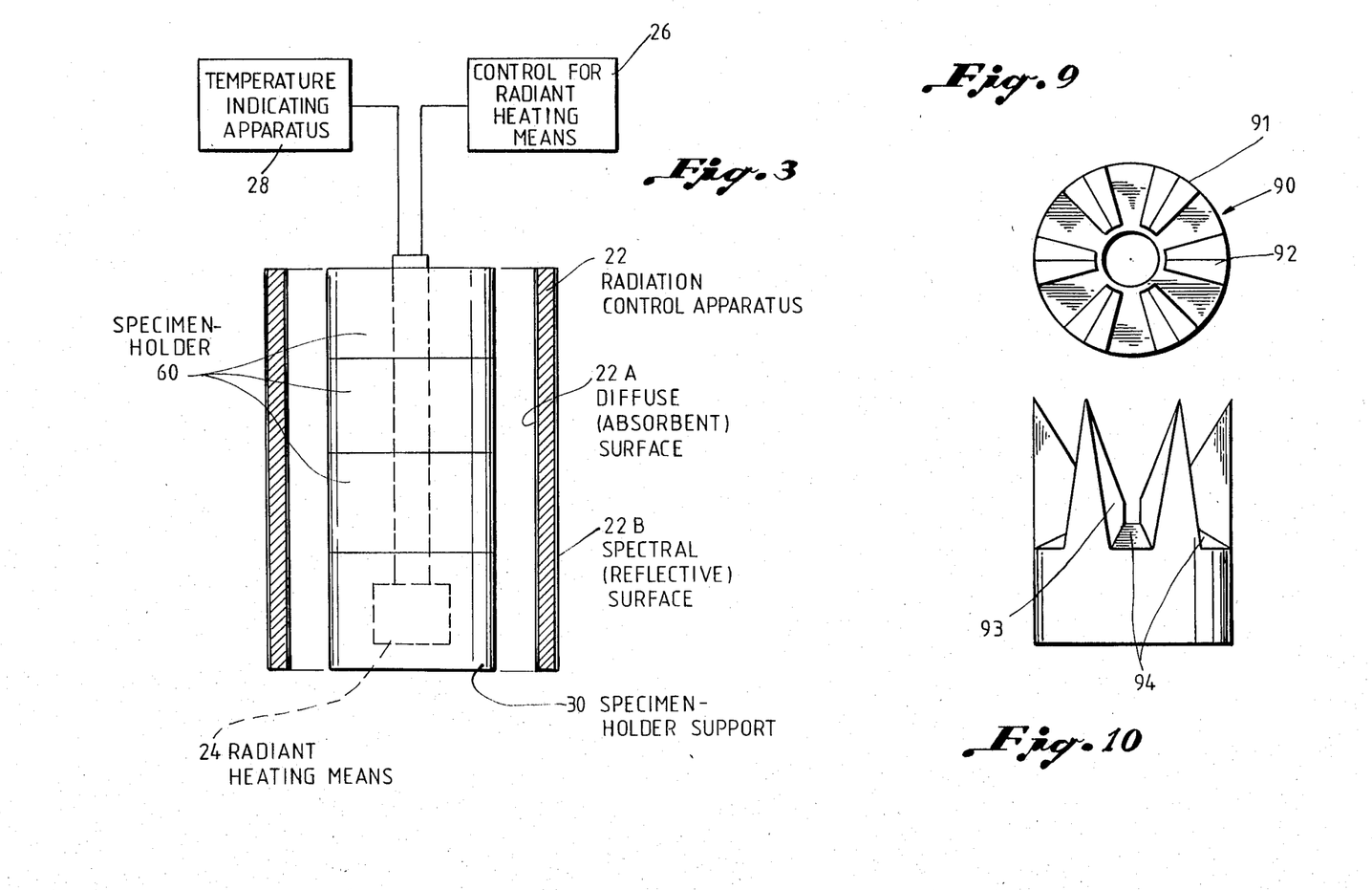
FIG. 3 is a schematic drawing of the sample chamber of this invention.
FIG. 9 is a top perspective view of the preferred radiant heater of this invention.
FIG. 10 is a side view in perspective of the preferred radiant heater of this invention.

The specimen holder illustrated in FIG. 3, also referred to herein as a sample holder, is unique to the practice of this invention. The sample holder must have the ability to retain tissue samples at cryotemperatures without adversely affecting those tissue samples. Preferably, the tissue samples are held in a suspended, isolated (no thermal conduction) condition. As can be seen from the schematic diagram, the sample holder contains rheostatically controlled heating elements which are monitered by constanton-Copper thermocouple temperature gauges. By the coordianted use of these materials, it is possible to control and monitor the approximate temperature of the tissue samples themselves.

Figures 1, 2:
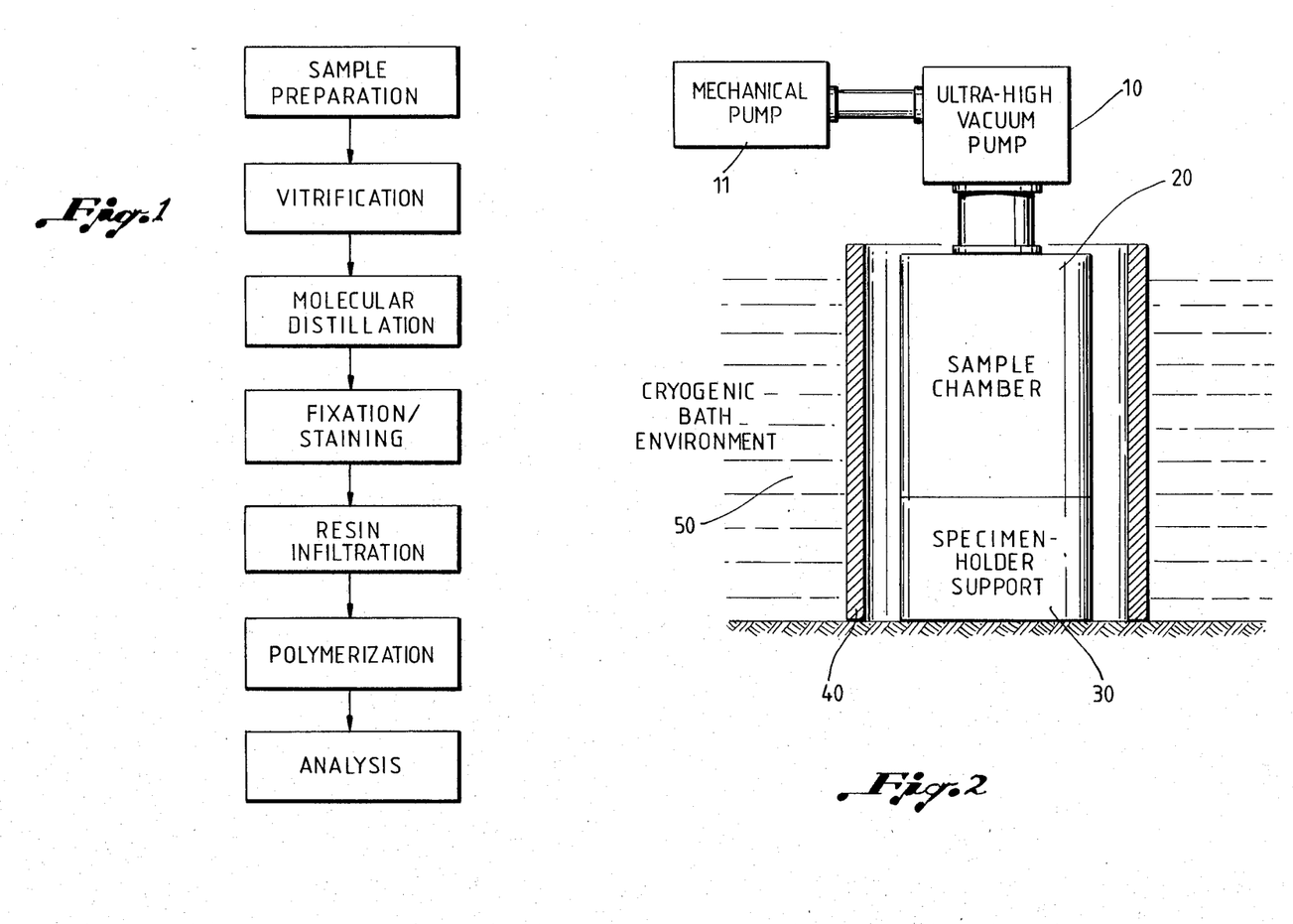
FIG. 1 is a schematic flow diagram of the method of this invention.
FIG. 2 is a schematic drawing of the apparatus of this invention.

The sample holder is contained within a cryostat or low temperature apparatus, which is in turn connected to a depressurization apparatus. The depressurization apparatus, as illustrated in FIG. 2, includes any of a variety of conventional apparati for obtaining and maintaining exceptionally low pressures. It should be noted that these are not conventional vacuum type pressures but are in fact simulation type depressurizations. The apparatus is one example of appropriate apparatus for use in the process of this invention to create the proper conditions for the thermal transfer required, although this should not be considered as limiting but merely as exemplary of the type of apparatus which have shown utility. As in many depressurization apparati, it is necessary that various suction means, motors, fans and heating elements be present in order to facilitate the proper functioning of the depressurization apparatus.

The rapid freezing attained by the apparatus of the Alan Boyne type is essential to the practice of the process of this invention. Conventionally, liquid nitrogen or other types of quenching baths in conjunction with chilling metal applications are used in the process of this invention to the extent they provide the vitrified phase of cell water. As illustrated schematically in FIG. 2, a liquid nitrogen quenching bath is used to lower and maintain the temperature of the tissue sample which is included in the tissue holder. It should be noted that while the tissue sample is maintained in the liquid nitrogen condition, it is necessary that tubulation access the various staining and fixation materials which are optionally preferred in the process of this invention, as well as the various resins which are ultimately used to embed the tissue samples of this invention prior to polymerization. Again, each of these functions is illustrated schematically in the attached figures. However, it should be understood that these are not intended to be limiting features of this invention but merely as illustrative of available technology.

In designing the apparatus or in selecting the apparatus for use in the process method of this invention, it is necessary to understand the effects of the exceptionally low temperatures and pressures on various materials. For that reason, portions of the apparatus of this invention used to treat the material while in the vitrified state are typically made from stainless steel. Other materials may well be equally viable. Likewise, portions of the apparatus of this invention are made from or coated with Teflon, a Dupont manufactured material which consists in a major portion of tetraflorans.

FIG. 2 illustrates schematically the apparatus used to practice the method of this invention. A mechanical pump 11 is attached to an ultra high vacuum pump 10. The vacuum apparatus 10 is connected to the sample chamber 20. The ultra high vacuum pump 10 can be any of a variety of commercially available vacuum pumping apparati. The preferred embodiment is a turbo molecular pump and in particular a turbo molecular pump manufactured by Leybold-Heraeus (Model TMP-360). It is essential that the ultra high vacuum pump, whether it is a turbo molecular pump or not, yield a hydrocarbon free vacuum. The mechanical pump 11 is used to pump out gases which are transmitted through the ultra high vacuum 10 from the sample chamber 20.

The sample chamber 20 is described and shown in more detail in FIG. 3. However, in FIG. 2 the sample chamber 20 is immediately adjacent to the specimen holder support assembly 30. The sample chamber 20 is used to retain the actual tissue samples. A thermal radiation shield 40 surrounds the sample chamber 20 to insulate the sample chamber 20 and the enclosed tissue samples from the ambient environment.

Typically the cryogenic bath environment 50 is liquid nitrogen contained by a dewar. The essential characteristic is that the temperature must not exceed $-140°$ C. The thermoconductivity of the cryogenic energy from the cryogenic bath environment 50 to the sample chamber 20 is inherent in the structure. There does not need to be any direct connection between the radiation shield 40 and the sample chamber 20 in order to maintain the appropriate temperature for the tissue samples.

FIG. 3 illustrates in more detail the sample chamber 20 and specimen holder support apparatus 30. The actual specimen holders are identified by the number 60. One or more of the specimen holders 60 are contained by the sample chamber 20. The specimen holders 60 are supported by support 30. The specimen holders are insulated from the surrounding environment by radiation control shield 22 which has an inside surface 22A which is diffuse (absorbent) and an exterior surface 22B which is spectral (reflective). In the preferred embodiment of this invention the surface 22A is totally black with emittance=0 (which will appear black) and completely absorbs any thermal radiation. Spectral surface 22B is highly polished to completely reflect any radiant energy. Coating exterior surface 22B with nickel or other material which can be highly polished is preferred.

Radiant heating means 24 are illustrated in FIG. 3 and provide a source of radiant heat to the tissue samples. Radiant heating means 24 are controlled by control means 26. Control means 26 permit infinite variability to the radiant heating means and typically are rheostats or thermostats. Temperature indicating means 28 is also connected to various points in the sample chamber assembly so that the temperature of the environment and tissue samples can be specifically controlled.

FIGS. 9 and 10 illustrate the preferred directional radiant heating means of this invention. In the preferred radiant heating means 24 as a result of proper alignment and manufacture the heat is transmitted in a virtually linear fashion as opposed to a random spherical radiant heat transmittance which is less efficient but is more typical. In this embodiment instead of the standard block of heating material as illustrated by the numeral 24 in FIG. 3 a specially designed block of heating material is used such as illustrated in FIGS. 9 and 10. In this embodiment raised portions 91 extend from the uppermost surface of preferred radiant heater 90. The surface 92 of raised portions 91 are highly polished such that the radiant heat is transmitted with as little loss of energy as possible and are specifically angled to provide the basis for virtually linear transmittance of radiant energy. Furthermore, and with reference particularly to FIG. 10 the grooved portion separating raised portions 91, identified herein as 93, is coated with a black material to give maximum energy transmittance.

In the most preferred embodiment of this invention the radiant heating means 24, control means 26 and temperature indicating means 28 are all operated by a computer within precise defined ranges.

Although FIG. 3 illustrates radiant heat, other forms of energy are equally useful in the apparatus and process of this invention. More particularly, electromagnetic energy sources such as microwaves, radio waves, acoustic sound waves, visual light waves and ultraviolet or near ultraviolet waves may be used. Magnetic flux is also useful, especially in combination with any of the above enumerated energy forms. Combinations of the above may be used depending on the application and sample to which the apparatus is placed. Infrared radiation should be avoided. Sample characteristics are of paramount importance in determining the energy source which is ultimately selected.

Figure 4:
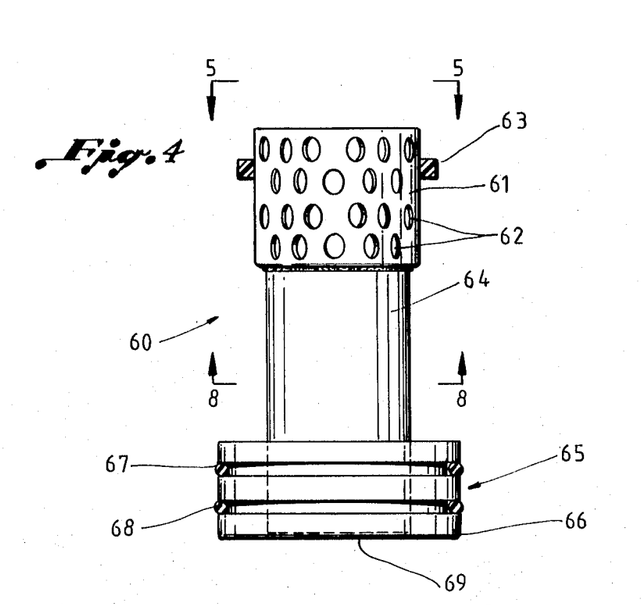
FIG. 4 is a side view of the specimen holder of this invention.

Referring now specifically to FIG. 4 the specimen holder assembly 60 is shown. A specimen chamber 61 is shown which is constructed typically of stainless steel. Apertures 62 may optionally be present in order to provide the basis for circulation of radiant energy as well as the removal of moisture. A spacing member 63 is preferably provided around the periphery of chamber 61. In its most preferred form spacer 63 is a Teflon 0-ring. Tubular support member 64 extends from the bottom of specimen chamber 61 and terminates in spacer member 65. Spacer 65 is preferably constructed of Teflon and consists of housing 66 and mated 0-rings 67 and 68. In the preferred embodiment the tubular support member 64 includes a desiccant material such as zeolite.

Figure 5:
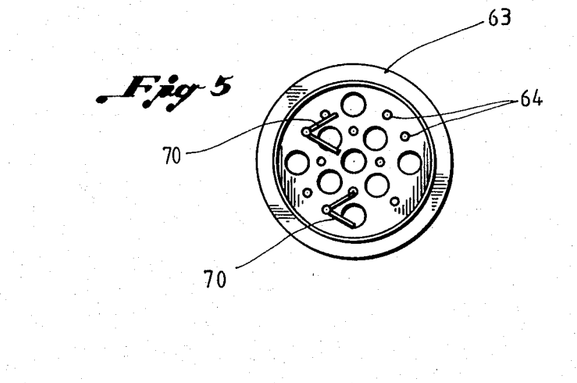
FIG. 5 is a top view of the specimen holder of this invention.

FIG. 5 is a top view of the specimen holder of this invention. The apertures 62 which are found in the sides of specimen chamber 61 are also bound in the bottom of the specimen chamber as illustrated by FIG. 5. These apertures permit the flow of moisture and transfer of radiant energy. A plurality of specimen spacers 70 are inserted into apertures 64 which are found throughout the bottom of specimen chamber 61. In the most preferred embodiment (see FIG. 7), the specimen spacers 70 have a downward extending leg 71 which is inserted into peripheral energy transfer members 80 as illustrated in FIG. 8 and which are contained and attached to the surface of tubular support member 64. Preferably, the members 80 consist of a Teflon tube with a tungsten wire running through the interior length of the member. The tubes are sized such that both the tungsten wire and the leg 71 of specimen spacers 70 are removably insertable into the interior of said member 80. In practice, the actual specimens are placed between adjoining specimen spacers 70. An infinite variety of shapes and configurations can be derived by use of specimen spacers 70. Thus the specimen holder of this invention is adaptable to virtually any type or size of tissue specimen.

Figure 7:
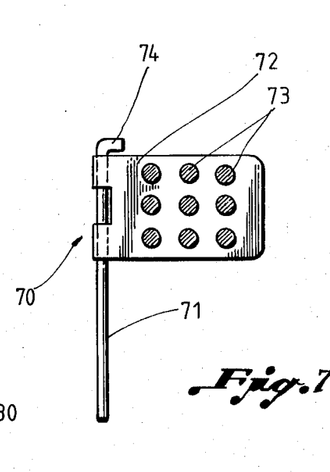
FIG. 7 is a perspective view of the specimen separation means of this invention.
Figure 8:
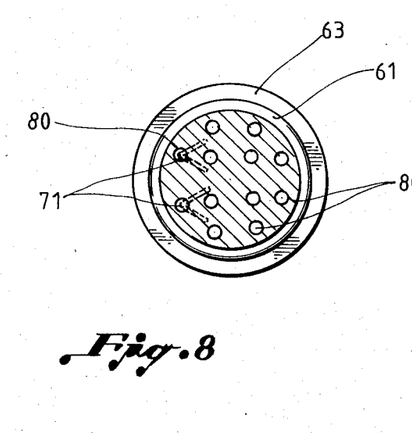
FIG. 8 is a section taken along line 8—8 of FIG. 4.

FIG. 7 illustrates the specimen spacer of this invention. In its preferred embodiment the specimen spacer 70 includes planar flanges 72 which have apertures 73 and which are pivotally mounted on retaining pin 74. Retaining pin 74 has a downwardly extending leg 71 which is insertable into tube 80. By inserting a plurality of the specimen spacers 70 into apertures 64 and in some instances into tubular member 80, a variety of configurations and arrangements of tissue specimens can be enjoyed.

Figure 6:
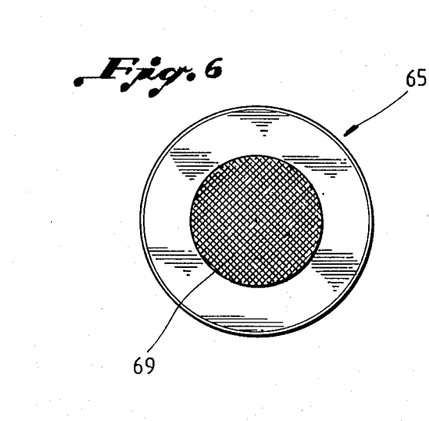
FIG. 6 is a bottom view of the specimen holder of this invention.

FIG. 6 illustrates the bottom of specimen holder 60 and in particular mesh 69. Teflon mesh 69 is provided to retain the zeolite or other desiccant material in tubular support member 64 while at the same time permitting the free-flow of moisture and the like through the bottom of said specimen holder 60.

Although the preferred embodiment of the specimen holder of this invention has been described herein above in some detail, it should be appreciated that a variety of embodiments will be readily available to a person designing an apparatus for a specific end use. The description of the preferred specimen holder of this invention is not intended to be limiting on this invention, but is merely illustrative of the preferred embodiment of this invention. Other specimen holders which incorporate modifications or changes to that which has been described herein and above are equally included within this application.

What is claimed is:

1. A method for cryopreparing a biological tissue sample for ultrastructural analysis comprising:
   (a) vitrifying a biological tissue sample;
   (b) depressurizing the atmosphere surrounding said sample;
   (c) bringing said vitrified tissue sample to equilibrium at a temperature of less than $-140°$ C.;
   (d) dehydrating said vitrified tissue sample while said sample is maintained in a state of equilibrium;
   (e) infiltrating said dehydrated tissue sample with a degassed resin;
   (f) polymerizing said resin in said infiltrated tissue sample to form an embedded tissue sample.

2. The method of claim 1 wherein said vitrifying is to a temperature of $-140°$ C. or below.

3. The method of claim 2 wherein said vitrifying is by means of liquid nitrogen.

4. The method of claim 3 wherein said vitrifying is completed in less than one second.

5. The method of claim 1 wherein said depressurizing is by means of drawing a vacuum on the atmosphere surrounding said tissue sample.

6. The method of claim 5 wherein said vacuum is at least $3 \times 10^{-9}$ Torr.

7. The method of claim 6 wherein said vacuum is created in less than 300 minutes.

8. The method of claim 1 wherein the equilibrium of said vitrified tissue sample is indicated by a constant temperature.

9. The method of claim 8 wherein said constant temperature is between $-140°$ C. to $-196°$ C.

10. The method of claim 1 wherein said dehydration is by means of sublimation.

11. The method of claim 10 wherein said dehydration is enhanced by the addition of energy from a secondary source.

12. The method of claim 11 wherein said secondary source of energy is heat energy.

13. The method of claim 11 wherein said secondary source of energy is radiant energy.

14. The method of claim 13 wherein said radiant energy is by means of nuclear magnetic resonance.

15. The method of claim 11 wherein said radiant energy is infrared produced by a laser and transmitted by fiber optics.

16. The method of claim 1 further comprising the addition of a contrast enhancing material.

17. The method of claim 16 wherein said contrast enhancing material is osmium tetraoxide.

18. The method of claim 1 wherein said polymerization is by heat.

19. The method of claim 1 wherein said polymerization is by means of ultraviolet light.

20. A method for cryopreparing a bilogical tissue sample for ultrastructural analysis comprising:
    (a) vitrifying a biological tissue sample by reducing the temperature of said sample to $-140°$ C. or below;
    (b) depressurizing the atmosphere surrounding said sample to less than $3 \times 10^{-9}$ Torr by drawing a vacuum, said vacuum to be drawn in less bhan 300 minutes;
    (c) bringing said vitrified tissue sample to equilibrium at a temperature of from $-140°$ C. to $-196°$ C.;
    (d) dehydrating said virified tissue sample, while said sample is maintained in a state of equilibrium, by sublimation or adiabatic molecular distillation;
    (e) adding a contrast enhancing material to said sample;
    (f) infiltrating said hehydrated tissue sample with a degassed resin; and
    (g) polymerizing said resin in said infiltrated tissue sample to form an embedded sample.

21. The method of claim 20 wherein said vitrifying is by means of liquid nitrogen.

22. The method of claim 21 wherein said vitrifying is completed in less than one second.

23. The method of claim 20 wherein said dehydration is enhanced by the addition of energy from a secondary source.

24. The method of claim 23 wherein said secondary source of energy is heat energy.

25. The method of claim 23 wherein said secondary source of energy is radiant energy.

26. The method of claim 23 wherein said radiant energy is by means of nuclear magnetic resonance.

27. The method of claim 23 wherein said radiant energy is infrared produced by a laser and transmitted by fiber optics.

28. The method of claim 20 wherein said contrast enhancing material is osmium tetraoxide.

29. The method of claim 20 wherein said polymerization is by heat.

30. The method of claim 20 wherein said polymerization is by means of ultraviolet light.

31. A method for cryopreparing a biological tissue sample for ultrastructural analysis comprising:
    (a) vitrifying a biological tissue sample by reducing the temperature of said sample to $-140°$ C. or below by the use of a liquid nitrogen bath;
    (b) depressurizing the atmosphere surrounding said sample to less than $3 \times 10^{-9}$ Torr in less than 300 minutes by drawing a vacuum on said sample;
    (c) bringing said vitrified tissue sample to equilibrium at a temperature of from $-140°$ C. to $-196°$ C.;
    (d) dehydrating said vitrified tissue sample, while said sample is maintained in a state of equilibrium, by sublimation or adiabatic moledular distillation and by the use of a secondary source of energy;
    (e) adding osmium tetraoxide to enhance the contrast of said tissue sample;
    (f) infiltrating said dehydrated tissue sample with a degassed resin; and
    (g) polymerizing said resin in said infiltrated tissue sample by adding heat.

* * * * *